(12) United States Patent
Kiguchi et al.

(10) Patent No.: US 8,940,795 B2
(45) Date of Patent: Jan. 27, 2015

(54) PLANT DISEASE CONTROLLING COMPOSITION AND METHOD FOR CONTROLLING PLANT DISEASE

(75) Inventors: So Kiguchi, Toyonaka (JP); Soichi Tanaka, Nishinomiya (JP); Mayuko Ozawa, Toyonaka (JP); Atsushi Iwata, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/580,906

(22) PCT Filed: Mar. 2, 2011

(86) PCT No.: PCT/JP2011/055431
§ 371 (c)(1),
(2), (4) Date: Aug. 23, 2012

(87) PCT Pub. No.: WO2011/108752
PCT Pub. Date: Sep. 9, 2011

(65) Prior Publication Data
US 2012/0322883 A1   Dec. 20, 2012

(30) Foreign Application Priority Data
Mar. 3, 2010   (JP) ................. 2010-046375

(51) Int. Cl.
*A01N 37/38* (2006.01)
(52) U.S. Cl.
CPC .................... *A01N 37/38* (2013.01)
USPC ............... 514/622; 514/365; 504/100
(58) Field of Classification Search
CPC ... A01N 37/38; A01N 2300/00; A01N 37/20; A01N 37/24
USPC ................... 504/100; 514/622, 365
See application file for complete search history.

(56) References Cited

U.S. PATENT DOCUMENTS

| | | | |
|---|---|---|---|
| 5,948,819 | A | 9/1999 | Ohtsuka et al. |
| 6,291,497 | B1 | 9/2001 | Schelberger et al. |
| 6,313,150 | B1 | 11/2001 | Ohtsuka et al. |
| 2002/0042437 | A1 | 4/2002 | Schelberger et al. |
| 2006/0281766 | A1 | 12/2006 | Tormo I Blasco et al. |
| 2008/0188530 | A1* | 8/2008 | Gewehr et al. ............ 514/365 |

FOREIGN PATENT DOCUMENTS

| CA | 2199422 A1 | 3/1996 |
|---|---|---|
| CN | 1257406 A | 6/2000 |
| CN | 1794913 A | 6/2006 |
| CN | 101617657 A | 1/2010 |
| EP | 1183948 A1 | 3/2002 |
| WO | WO 95/27693 A1 | 10/1995 |
| WO | WO 96/07633 A1 | 3/1996 |
| WO | WO 98/53684 A1 | 12/1998 |
| WO | WO 02/10101 A1 | 2/2002 |
| WO | WO 2009/119872 A2 * | 10/2009 ............ A01N 43/88 |
| WO | WO 2009/119872 A2 | 10/2009 |

OTHER PUBLICATIONS

Delp, C.; Title: Coping with Resistance to Plant Disease; Plant Disease, vol. 64 No. 7, pp. 652-657, published Jul. 1980 by American Phytopathological Society.*
Anonymous author, Title: Pesticide fact sheet: zoxamide, EAP registration data, year of initial registration, 2001.*
Anonymous author, Title: Pesticide registration revew: flutolanil, EAP registration review summary, 2008.*
International Preliminary Report on Patentability for International Patent Application No. PCT/JP2011/055431, dated Sep. 13, 2012.
PCT/ISA/210—International Search Report mailed on Jan. 23, 2012, issued in PCT/JP2011/055431.
PCT/ISA/237—Written Opinion of the International Searching Authority mailed on Jan. 23, 2012, issued in PCT/JP2011/055431.
Chinese Office Action for corresponding Chinese Application No. 201180012287.4 dated Aug. 29, 2013 (with English translation).
The Communication Pursuant to Article 94(3) EPC, dated Feb. 19, 2014, issued in the corresponding European Patent Application No. 11710038.8.
The Second Office Action (including English translation), dated Mar. 27, 2014, issued in the corresponding Chinese Patent Application No. 201180012287.4, English translation is considered.
The Office Action (including an English translation), dated Jun. 16, 2014, issued in the corresponding Mexican Patent Application No. MX/a/2012/009669.
The Pesticide Manual, 15th Edition, Published by British Crop Protection Council (BCPC), ISBN 1901396188, Nov. 2009 (6 pages).

* cited by examiner

*Primary Examiner* — Richard Schnizer
*Assistant Examiner* — Yanzhi Zhang
(74) *Attorney, Agent, or Firm* — Birch, Stewart, Kolasch & Birch, LLP

(57) ABSTRACT

The present invention provides a composition having an excellent controlling activity on plant disease. The composition comprising the compound represented by the formula (1) and one or more benzamide fungicidal compound selected from the group (A) shows an excellent controlling activity on a plant disease. group (A): a group consisting of flutolanil, mepronil, and zoxamide.

(1)

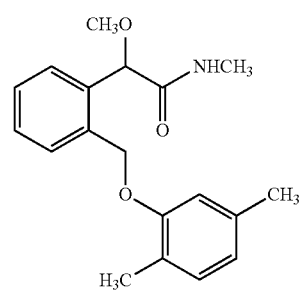

5 Claims, No Drawings

PLANT DISEASE CONTROLLING COMPOSITION AND METHOD FOR CONTROLLING PLANT DISEASE

TECHNICAL FIELD

The present invention relates to a plant disease controlling composition and a method for controlling a plant disease.

BACKGROUND ART

Hitherto, there has been provided compounds as an active ingredient for a composition for controlling plant disease (see e.g., The Pesticide Manual—15th edition (BCPC published) ISBN 1901396188).

Also there has been provided a compound of the formula (1):

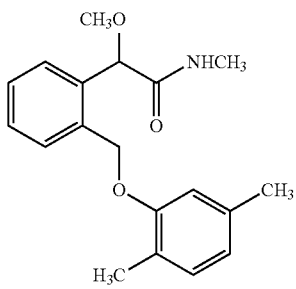

(see e.g., WO 95/27693 pamphlet and WO 02/10101 pamphlet).

DISCLOSURE OF INVENTION

An object of the present invention is to provide a composition having an excellent control effect on a plant disease.

The present inventors have intensively studied to find out a composition having an excellent control effect on a plant disease. As a result, they have found that a composition comprising a compound represented by the formula (1) and one or more benzamide fungicidal compound selected from the following group (A) shows a synergistic activity, and thus has an excellent control effect on a plant disease, and therefore the present invention has been completed.

The present invention provides:

[1] A plant disease controlling composition comprising a compound represented by the formula (1):

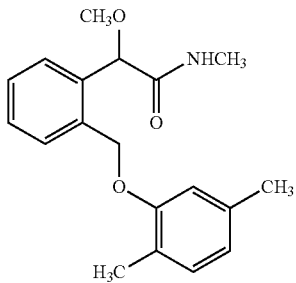

and one or more benzamide fungicidal compound selected from the following group (A):

group (A): a group consisting of flutolanil, mepronil, and zoxamide.

[2] The plant disease controlling composition according to the above [1], wherein a weight ratio of the compound represented by the formula (1) to the benzamide fungicidal compound is that of the compound represented by the formula (1)/the benzamide fungicidal compound=0.0125/1 to 500/1.

[3] The plant disease controlling composition according to the above [1] or [2], wherein the compound represented by the formula (1) is that represented by the formula (1) having R— absolute configuration.

[4] A method for controlling a plant disease which comprises applying each effective amount of the compound of the formula (1):

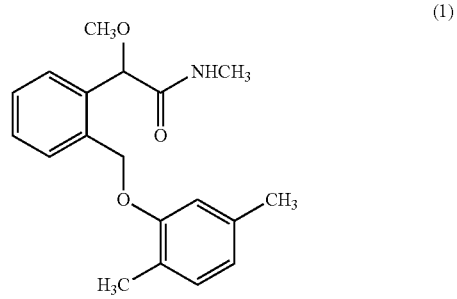

and one or more benzamide fungicidal compound selected from the following group (A) to a plant or a soil for cultivating the plant, group (A): a group consisting of flutolanil, mepronil, and zoxamide.

[5] The method for controlling a plant disease according to the above [4], wherein the plant or the soil for cultivating the plant is a seed.

[6] The method for controlling a plant disease according to the above [4] or [5], wherein a weight ratio of the compound represented by the formula (1) to the benzamide fungicidal compound is that of the compound represented by the formula (1)/the benzamide fungicidal compound=0.0125/1 to 500/1.

[7] The method for controlling a plant disease according to any one of the above [4] to [6], wherein the compound represented by the formula (1) is that represented by the formula (1) having R— absolute configuration.

[8] A use of a combination of the compound represented by the formula (1):

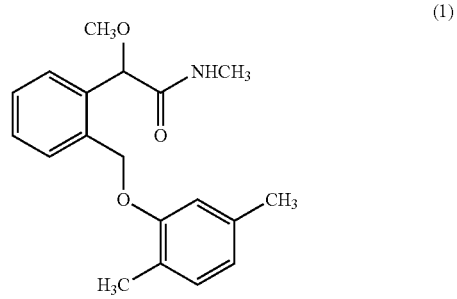

and one or more benzamide fungicidal compound selected from the following group (A) for controlling a plant disease, group (A): a group consisting of flutolanil, mepronil, and zoxamide.

The present invention enables to control a plant disease.

BEST MODE FOR CARRYING OUT THE INVENTION

A plant disease controlling composition of the present invention (hereinafter, referred to as a composition of the present invention) comprises a compound represented by the formula (1):

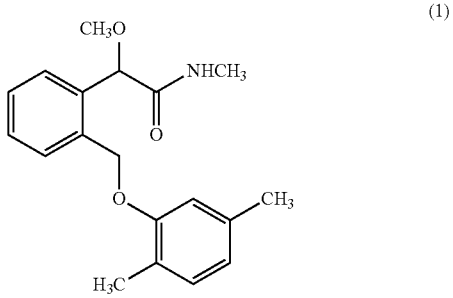

(hereinafter, referred to as an amide compound of the present invention) and one or more benzamide compound selected from the following group (A) (hereinafter, referred to as a benzamide compound of the present invention),
group (A): a group consisting of flutolanil, mepronil, and zoxamide.

The present amide compounds are those described in for example, WO 95/27693 pamphlet and WO 02/10101 pamphlet, and thus can be prepared according to the method described therein.

The present amide compound has one asymmetric carbon. Herein, a compound represented by the formula (1) wherein an enantiomer having R— absolute configuration is enriched is referred to as the amide compound having R— absolute configuration.

The present amide compound encompasses the following compounds:
a compound represented by the formula (1) which is contained an enantiomer having R— absolute configuration in 70% and more;
a compound represented by the formula (1) which is contained an enantiomer having R— absolute configuration in 90% and more;
a compound represented by the formula (1) which is contained an enantiomer having R— absolute configuration in 95% and more.

Flutolanil, mepronil, and zoxamide that used in the present invention are all known compounds, and are described in for example, "The PESTICIDE MANUAL—15th EDITION (BCPC published) ISBN 1901396188", pages 559, 729 and 1198 respectively. These compounds are either commercially available, or can be prepared by a known method.

The weight ratio of the present amide compound to the present benzamide compound in the composition of the present invention is usually that of the present compound/the present benzamide compound=0.0125/1 to 500/1, preferably 0.025/1 to 100/1, and more preferably 0.1/1 to 10/1.

Although the composition of the present invention may be a mixture as itself of the present amide compound and the present benzamide compound, the composition of the present invention is usually prepared by mixing the present amide compound, the present benzamide compound and an inert carrier, and if necessary, adding a surfactant or other pharmaceutical additives, and then formulating into the form of oil solution, emulsifiable concentrate, flowable formulation, wettable powder, granulated wettable powder, dust formulation, granules and so on. Such formulations can be used by itself or with an addition of other inert components as an agent for controlling a plant disease.

Usually, the composition of the present invention can contain 0.1 to 99% by weight, preferably 0.2 to 90% by weight, and more preferably 1 to 80% by weight of the present amide compound and the present benzamide compound in total.

Examples of a solid carrier used on the formulation include finely-divided power or particles of clay consisting of minerals (e.g., kaolin clay, attapulgite clay, bentonite, montmorillonite, acid clay, pyrophyllite, talc, diatomaceous earth, or calcite), natural organic substances (e.g., corncob powder, or walnut shell powder), synthetic organic substances (e.g., urea), salts (e.g., calcium carbonate, or ammonium sulfate), synthetic inorganic substances (e.g., synthetic hydrous silicon oxide) and so on. Examples of a liquid carrier include aromatic hydrocarbons (e.g., xylene, alkyl benzene, or methylnaphtalene), alcohols (e.g., 2-propanol, ethylene glycol, propylene glycol, or ethylene glycol monoethyl ether), ketones (e.g., acetone, cyclohexanone, or isophorone), vegetable oils (e.g., soybean oil, or cotton oils), petroleum-derived aliphatic hydrocarbons, esters, dimethylsulfoxide, acetonitrile and water.

Examples of the surfactant include anionic surfactant (e.g., alkyl sulfate salts, alkylaryl sulfate salts, dialkyl sulfosuccinate salts, polyoxyethylene alkylaryl ether phosphates, lignin sulfonate, or naphthalenesulfonate formaldehyde polycondensation), nonionic surfactant (e.g., polyoxyethylene alkylaryl ether, polyoxyethylene alkyl polyoxypropylene block copolymer, or sorbitan fatty acid ester) and cationic surfactant (e.g., alkyltrimethyl ammonium salts).

Examples of the other pharmaceutical additives include water-soluble polymer (e.g., polyvinyl alcohol, or polyvinyl pyrrolidone), polysaccharides (e.g. arabic gum, alginic acid and salts thereof, CMC (carboxymethyl-cellulose), or xanthan gum), inorganic substances (e.g, aluminum magnesium silicate, or alumina-sol), antiseptic agent, coloring agent, and PAP (isopropyl acid phosphate), and stabilizing agent (e.g., BHT).

The composition of the present invention can also be prepared by separately formulating the present amide compound and the present benzamide compound into different formulations by the above procedures, if necessary, further diluting each of them with water, thereafter, mixing the separately prepared different formulations or the dilute solutions.

The composition of the present invention may further contain one or more other fungicide and/or insecticide.

The composition of the present invention is used to control a plant disease by applying it to a plant or a soil for cultivating the plant.

The plant disease which can be controlled by the present invention is exemplified below:

Rice diseases: blast (*Magnaporthe oryzae*) helminthosporium leaf spot (*Cochliobolus miyabeanus*) sheath blight (*Rhizoctonia solani*) and bakanae disease (*Gibberella fujikuroi*);

Diseases of barley, wheat, oats and rye: powdery mildew (*Erysiphe graminis*) Fusarium head blight (*Fusarium graminearum, F. avenaceum, F. culmorum, F. asiatricum, Microdochium nivale*), rust (*Puccinia striiformis, P. graminis, P. recondite, P. hordei*), snow blight (*Typhula* sp., *Micronectriella nivalis*), loose smut (*Ustilago tritici, U. nuda*), bunt (*Tilletia caries*), eyespot (*Pseudocercosporella herpotrichoides*) scald (*Rhynchosporium secalis*), leaf blotch (*Septo-

*ria tritici*), glume blotch (*Leptosphaeria nodorum*) and net blotch (*Pyrenophora teres* Drechsler);

Citrus diseases: melanose (*Diaporthe citri*), scab (*Elsinoe fawcetti*) and Penicillium rot (*Penicillium digitatum, P. italicum*);

Apple diseases: blossom blight (*Monilinia mali*) canker (*Valsa ceratosperma*), powdery mildew (*Podosphaera leucotricha*), Alternaria leaf spot (*Alternaria alternata* apple pathotype), scab (*Venturia inaequalis*), bitter rot (*Colletotrichum acutatum*) and late blight (*Phytophtora cactorum*);

Pear diseases: scab (*Venturia nashicola, V. pirina*), black spot (*Alternaria* alternate Japanese pear pathotype), rust (*Gymnosporangium haraeanum*) and late blight (*Phytophtora cactorum*);

Peach diseases: brown rot (*Monilinia fructicola*), scab (*Cladosporium carpophilum*) and Phomopsis rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), downy mildew (*Plasmopara viticola*) and Gray mold (*Botrytis cinerea*);

Diseases of Japanese persimmon: anthracnose (*Gloeosporiura kaki*) and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Mycosphaerella melonis*), Fusarium wilt (*Fusarium oxysporum*), downy mildew (*Pseudoperonospora cubensis*) Phytophthora rot (*Phytophthora* sp.) and damping-off (*Pythium* sp.);

Tomato diseases: early blight (*Alternaria solani*), leaf mold (*Cladosporium falvum*) and late blight (*Phytophthora infestans*);

Egg plant disease: brown spot (*Phomopsis vexans*) and powdery mildew (*Erysiphe cichoracearum*);

Diseases of Cruciferous Vegetables: Alternaria leaf spot (*Alternaria japonica*), white spot (*Cercosporella brassicae*), clubroot (*Plasmodiophora brassicae*), and downy mildew (*Peronospora parasitica*);

Rapeseed diseases: Sclerotinia rot (*Sclerotinia sclerotiorum*), black spot (*Alternaria brassicae*), powdery mildew (*Erysiphe cichoracearum*), blackleg (*Leptosphaeria maculans*);

Welsh onion diseases: rust (*Puccinia aliii*);

Soybean diseases: purple seed stain (*Cercospora kikuchii*), *Sphaceloma* scad (*Elsinoe glycines*), pod and stem blight (*Diaporthe phaseolorum* var. *sojae*) rust (*Phakopsora pachyrhizi*) and phytophthora stem rot (*Phytophthora sojae*);

Adzuki-bean diseases: Gray mold (*Botrytis cinerea*), Sclerotinia rot (*Sclerotinia sclerotiorum*);

Kidney bean diseases: Gray mold (*Botrytis cinerea*), Sclerotinia rot (*Sclerotinia sclero tiorum*), anthracnose (*Colletotrichum lindemthianum*);

Peanut diseases: leaf spot (*Cercospora personata*), brown leaf spot (*Cercospora arachidicola*) and southern blight (*Sclerotium rolfsii*);

Garden pea diseases: powdery mildew (*Erysiphe pisi*);

Potato diseases: early blight (*Alternaria solani*) and late blight (*Phytophthora infestans*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.) and anthracnose (*Colletotrichum theae-sinensis*)

Cotton diseases: *fusarium* wilt (*Fusarium oxysporum*), damping-off (*Rhizoctonia solani*);

Tobacco diseases: brown spot (*Alternaria longipes*), powdery mildew (*Erysiphe cichoracearum*), anthracnose (*Colletotrichum tabacum*), downy mildew (*Peronospora tabacina*) and late blight (*Phytophthora nicotianae*);

Sugar beet diseases: *Cercospora* leaf spot (*Cercospora beticola*), leaf blight (*Thanatephorus cucumeris*), Root rot (*Aphanidermatum cochlioides*);

Rose diseases: black spot (*Diplocarpon rosae*) and powdery mildew (*Sphaerotheca pannosa*)

Chrysanthemum diseases: leaf blight (*Septoria chrysanthemi-indici*) and white rust (*Puccinia horiana*);

Various plants diseases: diseases caused by *Pythium* spp. (*Pythium aphanidermatum, Pythium debarianum, Pythium graminicola, Pythium irregulare, Pythium ultimum*), Gray mold (*Botrytis cinerea*), Sclerotinia rot (*Sclerotinia sclerotiorum*), Japanese radish diseases: *Alternaria* leaf spot (*Alternaria brassicicola*);

Turfgrass diseases: dollar spot (*Sclerotinia homeocarpa*), brown patch and large patch (*Rhizoctonia solani*); and Banana diseases: Sigatoka disease (*Mycosphaerella fijiensis, Mycosphaerella musicola, Pseudocercospora musae*).

Examples of the plants to which the composition of the present invention can be applied are as follows:

Crops: corn, rice, wheat, barley, rye, oat, sorghum, cotton, soybean, adzuki-bean, kindney bean, peanut, buckwheat, beet, rapeseed, sunflower, sugar cane, and tobacco, etc.;

Vegetables: solanaceous vegetables (eggplant, tomato, pimento, pepper, and potato, etc.), cucurbitaceous vegetables (cucumber, pumpkin, zucchini, water melon, melon, and squash, etc.), cruciferous vegetables (Japanese radish, white turnip, horseradish, kohlrabi, Chinese cabbage, cabbage, leaf mustard, broccoli, and cauliflower, etc.), asteraceous vegetables (burdock, crown daisy, artichoke, and lettuce, etc.), liliaceous vegetables (green onion, onion, garlic, and asparagus) ammiaceous vegetables (carrot, parsley, celery, and parsnip, etc.), chenopodiaceous vegetables (spinach, and Swiss chard, etc.), lamiaceous vegetables (*Perilla frutescens*, mint, and basil, etc.) strawberry, sweet potato, *Dioscorea japonica*, and colocasia, etc.;

Flowers;

Foliage plants;

Turfgrass;

Fruits: pomaceous fruits (apple, pear, Japanese pear, Chinese quince, and quince, etc.), stone fleshy fruits (peach, plum, nectarine, *Prunus* mume, cherry fruit, apricot, and prune, etc.), citrus fruits (*Citrus unshiu*, orange, lemon, lime, and grapefruit, etc.), nuts (chestnut, walnuts, hazelnuts, almond, pistachio, cashew nuts, and macadamia nuts, etc.), berries (blueberry, cranberry, blackberry, and raspberry, etc.), grape, kaki fruit, olive, Japanese plum, banana, coffee, date palm, and coconuts, etc.; and Trees other than fruit trees: tea, mulberry, flowering plant, roadside trees (ash, birch, dogwood, Eucalyptus, *Ginkgo biloba*, lilac, maple, *Quercus*, poplar, Judas tree, Liquidambar formosana, plane tree, zelkova, Japanese arborvitae, fir wood, hemlock, juniper, *Pinus, Picea*, and Taxus cuspidate), etc.

The aforementioned "plants" include plants which resistance has been imparted by genetic recombination.

Exemplary embodiments of the composition of the present invention are as follows:

a composition comprising the present amide compound and flutolanil wherein a weight ratio thereof is that of the present amide compound/flutolanil=0.0125/1 to 500/1;

a composition comprising the present amide compound and flutolanil wherein a weight ratio thereof is that of the present amide compound/flutolanil=0.025/1 to 100/1;

a composition comprising the present amide compound and flutolanil wherein a weight ratio thereof is that of the present amide compound/flutolanil=0.1/1 to 10/1;

a composition comprising the present amide compound and mepronil wherein a weight ratio thereof is that of the present amide compound/mepronil=0.0125/1 to 500/1;

a composition comprising the present amide compound and mepronil wherein a weight ratio thereof is that of the present amide compound/mepronil=0.025/1 to 100/1;

a composition comprising the present amide compound and mepronil wherein a weight ratio thereof is that of the present amide compound/mepronil=0.1/1 to 10/1;

a composition comprising the present amide compound and zoxamide wherein a weight ratio thereof is that of the present amide compound/zoxamide=0.0125/1 to 500/1;

a composition comprising the present amide compound and zoxamide wherein a weight ratio thereof is that of the present amide compound/zoxamide=0.025/1 to 100/1; and a composition comprising the present amide compound and zoxamide wherein a weight ratio thereof is that of the present amide compound/zoxamide=0.1/1 to 10/1.

The method for controlling a plant disease of the present invention (hereinafter, referred to as the method for controlling of the present invention) is carried out by applying each effective amount of the present amide compound and the present benzamide compound to the plants or the soil for cultivating the plant.

Such the plants may be, for example, foliages of plant, seeds of plant, or bulbs of plant. The bulbs herein are intended to mean bulb, corm, rootstock, tubera, tuberous root and rhizophore.

In the method for controlling of the present invention, the present amide compound and the present benzamide compound may be applied separately around the same time to the plant or the soil for cultivating the plant, but is usually applied as the composition of the present invention in terms of a convenience on applying.

In the method for controlling of the present invention, examples of the method of applying the present amide compound and the benzamide compound include foliage treatment, soil treatment, root treatment and seed treatment.

Such the foliage treatment includes for example, a method of applying the composition of the present invention to a surface of the plant to be cultivated by a foliage application or a stem application.

Such the root treatment includes for example, a method of soaking a whole or a root of the plant into a medicinal solution comprising the present amide compound and the present benzamide compound, and a method of attaching a solid formulation comprising the present amide compound, the present benzamide compound and the solid carrier to a root of the plant.

Such the soil treatment includes for example, soil broadcast, soil incorporation, and irrigation of the medicinal solution to a soil.

Such the seed treatment includes for example, an applying of the composition of the present invention to a seed or a bulb of the plant to be prevented from the plant disease, specifically, for example, a spray treatment by spraying a suspension of the composition of the present invention in a mist form to a surface of a seed or a surface of a bulb, a smear treatment by smearing the wettable powder, the emulsifiable concentrate or the flowable formulation of the composition of the present invention with added by small amounts of water or as itself to a seed or a bulb, an immerse treatment of a seed into a solution of the composition of the present invention for a given time, a film-coating treatment, and a pellet-coating treatment.

Each dose of the present amide compound and the present benzamide compound in the method for controlling of the present invention may be varied depending on a kind of plant to be treated, a kind or a frequency of an occurrence of a plant disease as a control subject, a dosage form, a treatment period, a treatment method, a treatment site, a climate condition, etc. In case of an application to a foliage of the plant or a soil for cultivating the plant, a total amount of the present amide compound and the benzamide compound is usually 1 to 500 g, preferably 2 to 200 g, and more preferably 10 to 100 g, per 1000 m². Each dose of the present amide compound and the present benzamide compound in the treatment for seed is usually 0.001 to 10 g, and preferably 0.01 to 1 g, per 1 kg of seeds.

The emulsifiable concentrate, the wettable powder or the flowable formulation, etc., is usually applied by diluting them with water, and then spreading them. In this case, usually, each concentration of the present amide compound and the present benzamide compound contain 0.0005 to 2% by weight, and preferably 0.005 to 1% by weight of the present amide compound and the present benzamide compound in total. The dust formulation or the granular formulation, etc, is usually applied as itself without diluting them.

EXAMPLES

Next, the present invention is described in more detail below by the following examples including formulation examples and a test example, but the present invention should not be construed to be limited thereto.

The formulation examples are given below. It is to be noted that in the formulation examples, the term "part" indicates "part by weight".

Formulation 1

5 parts of the present amide compound, 5 parts of flutolanil, 35 parts of a mixture of white carbon and polyoxyethylene alkylether sulfate ammonium salts (weight ratio 1:1), and 55 parts of water were mixed and the resulting solution was then subjected to fine grinding according to a wet grinding method, so as to obtain a flowable formulation. The same above operations were carried out with mepronil or zoxamide instead of flutolanil, so as to obtain various types of flowable formulations.

Formulation 2

10 parts of the present amide compound, 5 parts of flutolanil and 1.5 parts of sorbitan trioleate were mixed into 28 parts of an aqueous solution that contained 2 parts of polyvinyl alcohol, and the mixed solution was then subjected to fine grinding according to a wet grinding method. Thereafter, 45.50 parts of an aqueous solution that contained 0.05 parts of xanthan gum and 0.1 part of aluminum magnesium silicate was added to the resultant, and 10 parts of propylene glycol was further added thereto. The obtained mixture was blended by stirring, so as to obtain the flowable formulation. The same above operations were carried out with mepronil or zoxamide instead of flutolanil, so as to obtain various types of flowable formulations.

Formulation 3

10 parts of the present amide compound, 40 parts of flutolanil, 3 parts of calcium lignosulfonate, 2 parts of sodium lauryl sulfate, and 45 parts of synthetic hydrous silicon oxide were fully crushed and mixed, so as to obtain wettable powders. The same above operations were carried out with mepronil or zoxamide instead of flutolanil, so as to obtain various types of wettable powders.

The test examples are given below.

Test Example 1

True leaf of cucumber is punched out with cork borer to 13 mm in diameter to prepare a leaf disk. In 24 well microwell plate that is dispensed with 1 ml 0.8% water agar, the leaf disk is placed such that the upper side of the leaf is in an upward direction. Thereto is added 20 micro liter a testing solution prepared by mixing a dimethyl sulfoxide solution of the present compound (racemate) and a dimethyl sulfoxide solution of flutolanil to a predetermined concentration to treat the leaf disk.

After confirming that the testing medical solution is dried, conidium of gray mold fungus (*Botrytis cinerea*) is suspended into potato dextrose broth (DIFCO) in a density of about $10^5$ conidium/mL and is then subjected to a spray inoculation. After leaving to stand the leaf disk in a growth chamber set up at 15° C. for four days, an onset area on the leaf is measured and then calculated an onset area rate (hereinafter, referred to as an onset area rate of treated group).

The same operation is carried out with 20 micro liter water instead of 20 micro liter a testing medicine solution to calculate an onset area rate (hereinafter, referred to an onset area rate of non-treated group).

A preventive value is calculated from the above onset area rate of treated group and the onset area rate of non-treated group by the following equation:

Preventive value(%)=100×(*A*−*B*)/*A* wherein
A: an onset area rate of treated group
B: an onset area rate of non-treated group
The results are shown in Table 1.

TABLE 1

| | treatment concentration (ppm) | | preventive value (%) |
|---|---|---|---|
| | the present amide compound | flutolanil | |
| 1 | 2.5 | 0.5 | 97 |
| 2 | 1.0 | 5.0 | 92 |

Test Example 2

The same operations as described in Test Example 1 are carried out with zoxamide instead of flutolanil, so as to calculate a preventive value.

Also for comparison, the same operations as described in Test Example 1 are carried out with the exception that the testing medicine solution is substituted with a predetermined concentration of each dimethyl sulfoxide solution of the present compound (racemate) or zoxamide, so as to calculate respective preventive values.

The results are shown in Table 2.

TABLE 2

| | treatment concentration (ppm) | | preventive value (%) |
|---|---|---|---|
| | the present amide compound | zoxamide | |
| 1 | 2.5 | 0.5 | 100 |
| 2 | 1.0 | 5.0 | 100 |

TABLE 2-continued

| treatment concentration (ppm) | | preventive value (%) |
|---|---|---|
| the present amide compound | zoxamide | |
| 2.5 | — | 56 |
| 1.0 | — | 46 |
| — | 0.5 | 10 |
| — | 5.0 | 15 |

Next, the Reference Example is given below.

Reference Example

For comparison, the same operations as described in Test Example 1 are carried out with the exception that the testing medicine solution is substituted with a predetermined concentration of a dimethyl sulfoxide solution of flutolanil, so as to calculate a preventive value.

The results are shown in Table 3.

TABLE 3

| treatment concentration (ppm) flutolanil | preventive value (%) |
|---|---|
| 0.5 | 10 |
| 5.0 | 15 |

The invention claimed is:

1. A composition for controlling a fungus disease in a plant comprising a compound of formula (1):

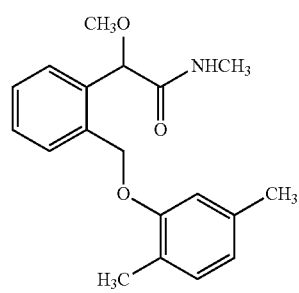

and one or more benzamide fungicidal compound selected from the following group (A):

group (A): a group consisting of flutolanil and zoxamide,
wherein a weight ratio of the compound of the formula (1) to the benzamide fungicidal compound is that of the compound of the formula (1)/the one or more benzamide fungicidal compound=0.1/1 to 10/1.

2. The composition according to claim 1, wherein the compound of the formula (1) is that of the formula (1) having R— absolute configuration.

3. A method for controlling a plant fungus disease which comprises applying each effective amount of a compound of formula (1):

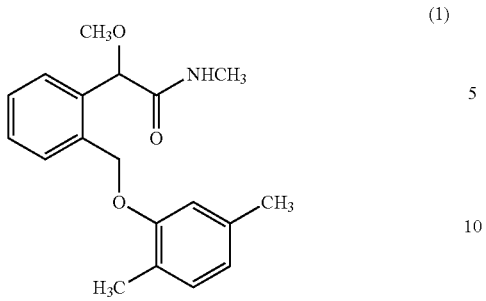 (1)

and one or more benzamide fungicidal compound selected from the following group (A) to a plant or a soil for cultivating the plant, group (A): a group consisting of flutolanil and zoxamide, wherein a weight ratio of the compound of the formula (1) to the benzamide fungicidal compound is that of the compound of the formula (1)/the one or more benzamide fungicidal compound=0.1/1 to 10/1.

4. The method according to claim 3, wherein the plant or the soil for cultivating the plant is a seed or a soil for cultivating a seed, respectively.

5. The method according to claim 3, wherein the compound of the formula (1) is that of the formula (1) having R— absolute configuration.

* * * * *